United States Patent
Braun et al.

(10) Patent No.: US 8,834,638 B2
(45) Date of Patent: Sep. 16, 2014

(54) CLEANING METHOD WITH IMPROVED LONG-TERM HYGIENE EFFECT

(75) Inventors: Markus Braun, Offenburg (DE); Thomas Peukert, Buehl (DE)

(73) Assignee: Meiko Maschinenbau GmbH & Co. KG, Offenburg (DE)

(*) Notice: Subject to any disclaimer, the term of this patent is extended or adjusted under 35 U.S.C. 154(b) by 530 days.

(21) Appl. No.: 12/761,975

(22) Filed: Apr. 16, 2010

(65) Prior Publication Data

US 2010/0263687 A1 Oct. 21, 2010

(30) Foreign Application Priority Data

Apr. 16, 2009 (EP) .................................. 09005409

(51) Int. Cl.
*B08B 7/04* (2006.01)
*A61G 9/02* (2006.01)
*A47L 15/00* (2006.01)
*A61L 2/18* (2006.01)
*A47L 15/42* (2006.01)

(52) U.S. Cl.
CPC ................ *A47L 15/0036* (2013.01); *A61G 9/02* (2013.01); *A61L 2202/14* (2013.01); *A61G 2203/46* (2013.01); *A47L 2401/34* (2013.01); *A47L 2501/30* (2013.01); *A61L 2202/17* (2013.01); *A47L 2501/26* (2013.01); *A61L 2/18* (2013.01); *A47L 15/0002* (2013.01); *A47L 2601/04* (2013.01); *A47L 15/4234* (2013.01)
USPC ................................ 134/18; 134/19; 134/25.2

(58) Field of Classification Search
None
See application file for complete search history.

(56) References Cited

U.S. PATENT DOCUMENTS

| | | | |
|---|---|---|---|
| 6,615,850 B1* | 9/2003 | Hornung | 134/57 R |
| 2008/0115807 A1 | 5/2008 | Gaus | |
| 2008/0283096 A1 | 11/2008 | Scheringer et al. | |

FOREIGN PATENT DOCUMENTS

| | | |
|---|---|---|
| DE | 10 2007 021 245 A1 | 11/2008 |
| WO | WO 2006/097294 A1 | 9/2006 |

* cited by examiner

*Primary Examiner* — Eric Golightly
(74) *Attorney, Agent, or Firm* — Muncy, Geissler, Olds & Lowe, P.C.

(57) ABSTRACT

A method for cleaning and/or disinfecting an item to be cleaned is proposed. The item to be cleaned is exposed to at least one cleaning fluid, heat equivalents to which the item to be cleaned is exposed being recorded. The heat equivalents are added up, the heat equivalents additionally being weighted with a compensation function during the summation of the heat equivalents. The compensation function can be a function of the temperature at which the heat equivalents were recorded. The compensation function can be adapted to provide heat equivalents recorded in at least one exceptional temperature range with a lower weighting than heat equivalents recorded in other temperature ranges.

15 Claims, 8 Drawing Sheets

PRIOR ART

PRIOR ART

CLEANING METHOD WITH IMPROVED LONG-TERM HYGIENE EFFECT

This nonprovisional application claims priority under 35 U.S.C. §119(a) to European Patent Application No. 09005409.9, which was filed on Apr. 16, 2010, and which is herein incorporated by reference.

BACKGROUND OF THE INVENTION

1. Field of the Invention

The invention relates to a method and a device for cleaning an item to be cleaned, and to a corresponding computer program. The cleaning method ensures in particular a thermal hygiene effect, in particular an improved long-term hygiene effect. The method can also be used to compensate for the so-called "lag of regrowth effect". Such cleaning methods and cleaning devices may be used for example in the natural sciences, technology, medicine or healthcare technology in order to subject various types of items to be cleaned to cleaning and hygienization, extending as far as disinfection. Application examples are dishwasher technology or the cleaning of healthcare utensils.

2. Description of the Background Art

In many fields of daily life, technology, the natural sciences and medicine and/or the healthcare sector, cleaning devices for a multiplicity of objects to be cleaned are known from the prior art. As examples, which do not however restrict the possible application scope of the present invention, dishwasher machines may be mentioned which are employed in the household sector or for example in the industrial sector as single-chamber or multiple-chamber dishwasher machines. As another example, cleaning devices for medical equipment and/or healthcare equipment may be mentioned, in particular containers which receive large amounts of liquid as waste. For example, cleaning-disinfection equipment may be mentioned here, which can be used for example to clean chamberpots, bedpans, urine bottles, night-time utensils or similar containers and instruments from the medical sector or healthcare sector.

Many cleaning devices are used to clean items to be cleaned, which come directly or indirectly in contact with possibly germ-laden materials. As examples to be mentioned here are objects which enter indirectly or directly in contact with the human body and can therefore act as transmitters of diseases, in particular infections, and for which particular value is therefore to be placed on sufficient hygienization, i.e. sufficient germ reduction, extending as far as disinfection.

Measuring and ensuring a hygiene level and/or germ reduction is the subject of many known methods and standards. In particular, with action of wet heat on the item to be cleaned, a relationship of temperature and time to the germ reduction in multiple-tank dishwasher machines has been studied. For example, DIN 10510 establishes minimum requirements for Germany in respect of temperature, cleaning-agent concentration and time between first contact of the item to be cleaned with the washing liquid until leaving the machine. The basis of this standard is the germ reduction of test bodies, contaminated in a defined way, after the cleaning process by means of so-called contact tests. In this test, *E. faecium* ATCC 6057 is used as a test germ or organism.

Testing the hygiene reliability of multiple-tank dishwashers at the end user is generally carried out by contact tests and determining the germ count in the wash water of the last washing tank. A disadvantage with this method, however, is the fact that testing of the germ reduction in situ at the customer according to this standard can only be carried out with great outlay. Another disadvantage of this standard is the fact that the same germ reduction could for example also be achieved with a shorter contact time but at higher temperatures in the individual treatment zones. The said standard does not allow for this.

Accordingly, there are standards which determine the hygienization effect of the cleaning equipment by means of cumulative heat equivalents. As explained in more detail below, heat equivalents generally refer to integrals or sums over a time profile of the temperature or a function value of a monotonically increasing function of the temperature, to which the item to be cleaned is exposed. The temperature is conventionally weighted according to an established weighting function or converted directly into weighted values.

In the USA, for example, the relationship of temperature and time to the germ reduction is described by the so-called NSF3 standard method. The basis of this specification is the germ reduction, determined from tests, of tuberculosis bacteria by the effect of temperature over time. The effect of temperature over time is referred to as a heat equivalent. In this method, a table records how many heat equivalents are achieved at which temperature. As a minimum temperature beyond which heat equivalents are counted, a temperature of 62° C. (corresponding to 143° F.) is mentioned according to this standard. For dishwashers, this usually means that at least 3600 heat equivalents must be reached according to this specification in order to fulfil the required germ reduction. An advantage of this method is that the method can be carried out in situ with relatively little outlay, in order to check correct functioning of a dishwasher machine in respect of thermal hygienization.

There are also corresponding standards in Germany and Europe. For example, for cleaning-disinfection equipment, EN ISO 15883-1 describes a method which is used to assess the hygiene effect likewise in the relationship between the germ reduction and the temperature over time. This relationship is also referred to as the $A_0$ value, and is likewise recorded in tabular form or calculated from a mathematical formula. The $A_0$ value is described in more detail in Annex A of this standard, and is defined as the time equivalent in seconds at 80° C. for which a given disinfection effect is exerted; it corresponds in essence to the procedure in the NSF3 standard but while being based on a different test germ.

The $A_0$ concept was developed in the scope of the European standardization work for disinfection methods. It came from the desire to make the efficacy control of thermal disinfection methods more transparent and the approval of disinfected items independent of microbiological control cultures (parametric approval). The $A_0$ concept is based on the assumption that a defined amount of energy, defined by temperature and action time, is necessary for the reproducible inactivation of a particular microbe load. This is in analogy with the F concept for the thermal sterilization of medical items, although in that case much higher amounts of energy are necessary than for disinfection. The $A_0$ concept involves assumptions which were made on the basis of empirical values concerning the thermal killing of microbes. The experimental bases, however, are sketchy and sometimes contradictory. A systematic experimental verification of the assumptions of the $A_0$ concept with different microbe classes has not yet been carried out.

According to the standard EN ISO 15883-1 (cleaning and disinfection equipment—Part 1: General requirements, definitions and tests), thermal disinfection with wet heat in cleaning and disinfection equipment (CDE) is defined and monitored parametrically by means of the $A_0$ value. This represents the applied energy as a product of applied temperature and action time. Biological indicators as time-consuming and variable "measuring sticks" for approval of the item to be disinfected are therefore largely obviated and replaced by registering physical parameters. The starting point is the A value, which represents a time equivalent in seconds at 80° C. for which a given disinfection effect is achieved. The following measurement units are important for the $A_0$ concept:

The microbiological parameter referred to as decimal reduction time or D value, as a measure which characterizes the thermal death behaviour of microorganisms. The D value indicates the time which is necessary to kill 90% of the microorganisms of a population at a given temperature T, i.e. to reduce the population to 10% of the initial number. The D value therefore represents a measure of the heat sensitivity of a particular microorganism type.

The dependency of the D value on the temperature T is recorded by a z value. The z value indicates the temperature increase which is necessary in order to reduce the D value by %10, i.e. to achieve the same killing effect in one tenth of the time.

The $A_0$ value is the A value for microorganisms whose z value is 10° C.; for the $A_0$ concept, the assumption is z=100 C. This assumption, together with the basic thesis that the same disinfection effect can be achieved both by higher temperature and shorter action time, and by lower temperature and correspondingly longer action time, gives a well-reproducible and practicable concept for dealing with thermal disinfection methods.

In EN ISO 15883-1, $A_0$ values of 60, 600 and 3000 are proposed for practical purposes, depending on the importance of the freedom from germs; an $A_0$ of 3000 means 50 times the amount of energy compared with an $A_0$ of 60 and achieves a much better disinfection effect. Table 1 presents examples of temperatures and times for the respective $A_0$ values.

TABLE 1

Time equivalents for various $A_0$ values.

| Temperature | $A_0$60 | $A_0$600 | $A_0$3000 |
| --- | --- | --- | --- |
| 70° C. | 10 min | 100 min | 500 min |
| 75° C. | 3.2 min | 32 min | 160 min |
| 80° C. | 1 min | 10 min | 50 min |
| 85° C. | 0.3 min | 3.2 min | 16 min |
| 90° C. | 6 s | 1 min | 5 min |
| 93° C. | 3 s | 30 s | 2.5 min |

From the conventional art, various cleaning devices are known which monitor the thermal hygienization of items to be cleaned according to one or more standards. For example, WO 2006/097294 A1, which corresponds to U.S. Publication No. 20080115807, which is incorporated herein by reference, describes a method for evaluating and ensuring the thermal hygiene effect in a continuous dishwasher. Permanently fitted in the continuous dishwasher, there are one or more sensors which record the temperature inside individual treatment zones and communicate them to a machine controller. The machine controller determines the thermal hygiene effect by means of the temperature and time respectively acting on the item to be cleaned, with the aid of heat equivalents. The washing process can be controlled so that a preset amount of heat equivalent values is applied to the item to be cleaned.

DE 10 2007 021 245 A1, which corresponds to U.S. Publication No. 20080283096, and which is incorporated herein by reference, proposes a disinfection controller for target pathogen selection. Information concerning a target germ, with which the object to be cleaned could be contaminated, is received and at least one process parameter is selected so that the target germ is killed with high probability in the cleaning process. The cleaning process is then carried out with the process parameter.

In practice, however, when using hygienization methods which are based on the recording of heat equivalents, for example according to one or more of the said standards, it has been found that the predicted hygienizations do not occur in all cases. In particular, it has been found that items to be cleaned, for example crockery, which should actually have a particular hygiene level according to the theoretical predictions of the standards, in fact have a lower hygiene level. It has furthermore been found that the measured hygiene level can sometimes depend strongly on the time which has elapsed between the hygienization and the measurement.

SUMMARY OF THE INVENTION

It is therefore an object of the present invention to provide a cleaning method and a cleaning device, which avoid the disadvantages of known devices and methods. In particular, the intention is also to be able to ensure longer-lasting and improved hygienization.

A method for cleaning and/or disinfecting items to be cleaned, and a cleaning device for cleaning and/or disinfecting items to be cleaned, are provided; the method can be carried out by using a cleaning device according to an embodiment of the invention, and the cleaning device can be adapted to carry out a method according to any of the described embodiments. Accordingly, for example, for possible configurations of the cleaning device reference may be made to the description of possible configurations of the method, and vice versa. The method and the device may for example be used for the purpose of cleaning or for example for the purpose of disinfection (i.e. germ reduction) or both purposes together, and may be adapted accordingly. A computer program having program code is furthermore provided, which is adapted to carry out the method in one or more of the described embodiments when the program is run on a computer, for example a computer of a cleaning device, for example a controller of a cleaning device. Carrying out may logically also be interpreted as controlling, so that the method may for example be adapted to make a cleaning device carry out the individual method steps when the program is run on a computer of the cleaning device, for example a computer in a controller of the cleaning device. The computer program may, in particular, be stored on a machine-readable medium.

The proposed cleaning method is based on fundamental considerations and studies of conventional standards, which are based on the recording and cumulation of heat equivalents. For example, the conventional $A_0$ value method evaluates the disinfection effect on the basis of a temperature-time integral or thermoequivalents, or cumulative thermoequivalents. Countable, i.e. effective units of thermoequivalents are in this case recorded beyond a temperature of 65° C. Upwards, there is generally a limitation only by practical and purely technical restrictions. Low temperatures are evaluated as less effective than higher values, by giving them a lower function value of a weighting function. The calculation of the disinfection effect may, for example, be carried out by solving corresponding $A_0$ value equations or by integration with a known temperature function. In practice, temperature equivalents of discrete time segments are often calculated and added up. In this case, however, the assumption is generally made that all thermoequivalents which are recorded at temperatures of at least 65° C. are in principle to be considered effective, albeit with a different weighting. Accordingly, it is unimportant whether a particular thermoequivalent and a particular $A_0$ value are achieved at higher or lower temperatures. Only the time necessary for this, i.e. a process parameter, makes the difference. Similar considerations also pertain for cumulative thermoequivalent values according to the NSF3 standard.

In practice, however, in various studies it has been found that the assumption of effectiveness beyond a minimum temperature specified for the corresponding thermoequivalent standard (for example 65° C. for EN ISO 15883 or 62° C. (corresponding to 143° F.) for NSF3) does not seem to be valid without exception for different microorganisms and process parameters. Thus the effect already indicated above, which is also referred to as "lag of regrowth", is to be observed in particular cases. This refers to a phenomenon in which microorganisms, for example microorganisms other than those which are used in the said standards, initially seemed to die and/or seem to be reduced at particular temperatures in the manner expected for the process parameters.

To this extent, the predictions of the corresponding standards are initially valid. After a very much longer resting time has elapsed, for example a resting time of from a few hours up to a few days or even a few weeks, however, the same microorganisms have an increasing vitality and can multiply again more. To this extent, it is found that in many cases at least some of the microorganisms have not actually died, but are merely inactivated and suggest death owing to lack of multiplication.

For the practice of disinfection, for example in cleaning devices, however, this means that items to be cleaned can have considerable differences in long-term behaviour even with the same cleaning level determined according to the standards. These differences are due to the fact that although in the end the item to be cleaned was exposed to the same cumulative number of thermoequivalents, this was possibly done with different process parameters, i.e. in particular different temperatures and with different treatment times, in order to reach these cumulative thermoequivalents. These differences, however, entail a different behaviour of the item to be cleaned in respect of the "lag of regrowth effect". Thus, in particular, the long-term behaviour of an item to be cleaned, for which a particular $A_0$ value or a particular value according to the NSF3 standard has been reached, may very well be dependent on the temperature prevailing at least for a time during the disinfection process. Furthermore, the microorganisms specifically to be reduced may also differ greatly in their long-term behaviour, even if the specific type of microorganism was taken into account for calculating the $A_0$ value, so that there is initially the same hygienization level or disinfection level after the cleaning process. An accurately defined hygienization level, for example an $A_0$ value, can thus also represent different hygiene results, particularly in respect of long-term behaviour.

Owing to these considerations according to the invention, the invention is based on the fact that cleaning processes, which have a hygienization and/or disinfection effect, should be controlled so that the risks due to vitiation of the hygiene result can be excluded. It should in this case also be possible to take into account specific discoveries concerning the effect of temperature influences on particular microorganisms, in particular the aforementioned "lag of regrowth effect". Accordingly, it should be possible to carry out the method in such a way that it initially performs hygienization on the basis of cumulative heat equivalents, so that for example at least a predetermined disinfection level, for example a predetermined $A_0$ value, can be reached. To this extent, the proposed method should satisfy conventional standards. At the same time, however, the method should be capable of compensating for the effects described above, which are caused by the specific time profile of the cumulation of heat equivalents and/or the special properties of particular microorganisms. To this extent, for example, adapted control of the process should be possible.

A method for cleaning and/or disinfecting an item to be cleaned is therefore provided, in which the item to be cleaned is exposed to at least one cleaning fluid. A cleaning device for cleaning items to be cleaned is furthermore provided, wherein the cleaning device comprises at least one controller for controlling a cleaning process, and the cleaning device is adapted to carry out a method in one or more of the forms described below. The controller may for example comprise one or more electronic and/or electromechanical components, and may in particular comprise one or more data-processing devices and/or networks of data-processing devices, for example one or more computers and/or microcontrollers. The controller may furthermore comprise for example input and output means, for example in order to allow a user and/or another computer or computer network to input commands and/or data into the controller and/or in order to be able to deliver information and/or data to the user and/or the other computer and/or the computer network. The controller may furthermore comprise one or more volatile and/or nonvolatile data memories.

In principle, a very wide variety of types of items to be cleaned may be used. The item to be cleaned may particularly preferably be an item to be cleaned which comes directly or indirectly in contact with food and/or drinks and/or is used for the preparation or provision of food and/or drinks, for example plates, cups, trays, cutlery, bowls, glasses or the like. Accordingly, the cleaning device may for example be configured as a dishwasher machine and/or comprise such a dishwasher machine. In this case, household dishwasher machines or industrial dishwasher machines may be modified according to the invention. The dishwasher machine may, for example, be configured as a single-chamber or multiple-chamber dishwasher machine. In particular, continuous dishwasher machines, in which the item to be cleaned is transported by means of a transport device through one or more cleaning zones, may be configured according to the invention.

As an alternative or in addition, other types of items to be cleaned may also be cleaned. In particular, the method may therefore also be used to clean medical equipment and/or healthcare equipment. In particular, the healthcare in equipment may comprise vessels which are adapted to receive sizeable quantities (for example more than 100 ml) of human excretion, for example bedpans, chamber pots, urine bottles or similar vessels. Another type of item to be cleaned may in principle also be cleaned. To this extent, the cleaning device may, for example, comprise one or more pieces of cleaning and disinfection equipment.

Cleaning, which may be carried out in the scope of the method and/or by using the said cleaning device in the cleaning method, may in particular be taken to mean removal of adhering contaminants. The said method, as explained in more detail below, furthermore involves a hygienization effect, hygienization generally being intended to mean germ reduction, extending as far as disinfection, i.e. a defined, at least almost complete killing of germs.

In order to expose the item to be cleaned to the at least one cleaning fluid, the method may in particular be carried out by using one or more cleaning chambers, or the cleaning device may comprise one or more such cleaning chambers, all or some of which may be configured as closed cleaning chambers, although all or some of them may also be configured as open cleaning chambers, for example cleaning tunnels. In principle, however, cleaning devices without such cleaning chambers are also possible. In order to apply the cleaning fluid, one or more nozzles may for example be used. Single-jet nozzles, multi-jet nozzles or nozzles configured in a different way, which may for example be contained in the at least one cleaning chamber, may in this case be used.

A cleaning fluid may be taken to mean any fluid medium, i.e. a liquid and/or a gas, which at least assists the cleaning process. In particular, the at least one cleaning fluid may comprise an aqueous cleaning-agent solution, i.e. a solution to which a quantity of at least one cleaning agent is added. In this regard, reference may be made to commercially available cleaning-agent solutions, as are used for example in cleaning-disinfection equipment and/or dishwasher machines. As an alternative or in addition, cleaning may also be carried out for example with plain water, for example in a secondary wash process in a dishwasher machine and/or in cleaning-disinfection equipment. A rinse aid may also for example be added to the fresh water, for example in order to facilitate drying of crockery, in particular glasses. Rinsing may for example be configured as pumped rinsing and/or as fresh water rinsing. Again as an alternative or in addition, the cleaning fluid may also comprise a vapour, for example steam. To this end, the cleaning device may for example comprise one or more steam generators, so that the item to be cleaned can be exposed to steam. Furthermore, the cleaning process, which may also comprise the method according to the invention, may also be configured so that a plurality of steps are carried out in succession, which may for example also comprise a plurality of steps in which the item to be cleaned is exposed to different types of cleaning fluid. In cleaning-disinfection equipment, for example, spraying of the vessels may initially be carried out after emptying the vessels, followed by optional cleaning with a cleaning-agent solution, in turn optionally followed by a steam sterilization step in which the vessels are hygienized with steam, extending as far as disinfection or sterilization. In dishwasher machines, for example, optionally a prewash, optionally a main wash and/or optionally one or more secondary wash or rinse steps may be combined with one another.

In general, the method can be carried out so that the item to be cleaned is exposed to wet heat by means of the at least one cleaning fluid, the cleaning fluid preferably being at a temperature lying above room temperature. For example, the cleaning fluid may be at a temperature in a range of between 60° C. and 100° C.

The method can be carried out by recording and adding up heat equivalents to which the item to be cleaned is exposed. The recording may for example take place during and/or immediately after exposing the item to be cleaned to the at least one cleaning fluid, so that the heat equivalents can be the heat equivalents which are transferred from the cleaning fluid to the item to be cleaned.

Heat equivalents can be intended to mean, for example, temperatures to which the item to be cleaned is exposed at a time and/or over a period of time, and which are weighted with a weighting function in order to assess their hygienization effect. This weighting function may in particular be a monotonically increasing weighting function, which converts the temperature of the item to be cleaned into a corresponding function value which characterizes the germ-killing effect. By means of the weighting function, the temperature may thus be multiplied by monotonically increasing weighting factors and/or the temperature may be fully replaced by function values increasing monotonically with the temperature. As examples of such weighting functions, reference may be made to the said standards. For example, reference may be made to Annex A of the NSF3 standard, in which heat equivalents are given as so-called HUE values in tables as a function of temperature and/or Annex A of Part 1 of the standard EN ISO 15883, in which corresponding weighting functions for converting the temperature of the item to be cleaned into corresponding heat equivalents are likewise specified. Examples will be explained in more detail below.

In the scope of the method according to the invention, the heat equivalents can be added up so that cumulative heat equivalents are considered, as for example also in the NSF3 and/or EN ISO 15883 standard, which may for example be used. The term adding up and the term cumulation will be used at least substantially synonymously below. The adding up may for example be carried out over discrete time segments, for example time segments of one second, as is proposed in the NSF3 standard. Since the time segments can in principle be selected to be arbitrarily small, in the limiting case this adding up of the heat equivalents may comprise integration of the heat equivalents as a function of time. As will be mentioned in more detail below, however, in contrast to known methods the adding up may be carried out with a not necessarily mathematically functional weighting function and/or controlled low-weighting and/or devaluation of a particular temperature range.

To this extent, the said method may initially correspond for example fully or partially to the methods described in WO 2006/097294 A1 or in DE 10 2007 021 245 A1, in which heat equivalents are likewise cumulated. In order to record the temperatures, for example, one or more temperature sensors which for example record the temperature directly on the item to be cleaned and/or other at other positions in the cleaning device, for example in one or more tanks for providing cleaning fluid, may be provided in the cleaning device. For example, the temperature sensors may comprise one or more temperature-dependent resistors and/or other types of temperature sensors, for example infrared optical temperature sensors. Recording the temperature directly on the item to be cleaned is particularly preferred. The one or more temperature sensors may, for example, be connected to the controller of the cleaning device and/or fully or partially be a component of this controller, so that the temperature signals can for example be delivered directly to the controller. In this case, for example, preprocessing of the temperature signals may be carried out so that, for example, they are filtered and/or already at least partially converted into heat equivalents.

However, the invention also proposes to allow compensation for deviations of known germ killing standards or disinfection standards, for example deviations owing to the described "lag of regrowth effects". Other, for example target germ-specific effects, may also be taken into account.

Accordingly, the invention proposes to weight the heat equivalents additionally with at least one compensation function. Such weighting may, for example, be taken to mean converting the heat equivalents into function values of the compensation function and/or, which is preferred in the scope of the present invention, simple multiplication of the heat equivalents by compensation values. The compensation function is in this case a function of the temperature at which the heat equivalents were recorded, and is adapted to provide heat equivalents recorded in at least one exceptional temperature range with a lower weighting than heat equivalents recorded in other temperature ranges. The compensation function need not necessarily be a function in the mathematical sense, but may for example also be an allocation, for example a relation and/or a list and/or a table, of compensation values as weighting factors. This will be explained in more detail below.

The temperature is therefore used twice in the scope of the method according to the invention, i.e. on the one hand to calculate the heat equivalents and on the other hand for additional weighting of the heat equivalents in order to compensate for example for "lag of regrowth effects". The exceptional temperature range may for example comprise one or more open and/or semi-open and/or closed temperature intervals. For example, these may be temperature intervals for which, although successful germ killing initially takes place within them, undesired effects can nevertheless occur later, for example the above-described "lag of regrowth effects". In such exceptional temperature ranges, which may for example be determined experimentally, for example for one or more target germs specified by a user and/or another computer or computer system, a lower weighting of the heat equivalents may be carried out than in other temperature ranges, for example in temperature ranges in which, as may be determined experimentally, "lag of regrowth effects" do not occur or occur only to a lesser extent.

The compensation function may in particular be adapted so that heat equivalents which have been recorded in the at least one exceptional temperature range are not taken into account in the summation. This may for example be done by multiplying the heat equivalents in this exceptional temperature range by a factor 0. Heat equivalents outside this exceptional temperature range, i.e. heat equivalents which have been recorded in other temperature ranges, may however be multiplied for example by factors greater than zero, for example a factor of one. Accordingly, the compensation function may for example comprise a simple digital function. Thus, the compensation function may be adapted so that the compensation function or the function value of this compensation function assumes a value of less than one for temperatures inside the exceptional temperature range, in particular a value of between zero and one, and in particular the value zero, and the value 1 for temperatures outside the exceptional temperature range. In this way, in particular, it is possible to ensure that a predetermined disinfection level, for example a predetermined cumulative value of heat equivalents, is at least reached in the method according to the invention. The method according to the invention may thus be carried out so that in every case it can satisfy current standards, for example the aforementioned standards, so that for example at least one $A_0$ value is reached. To this extent, without specified standards being infringed against, the proposed method may also be integrated without great adaptations into existing cleaning devices.

The at least one exceptional temperature range, or the compensation function, may be configured in different ways. One possibility is at least one exceptional temperature range or, when a plurality of exceptional temperature ranges are provided, one of these exceptional temperature ranges being arranged at the lower end of the temperature range beyond which heat equivalents are counted. Thus, the exceptional temperature range or one of the exceptional temperature ranges may for example extend between a minimum temperature of a standard used for recording the heat equivalents and at least one predetermined regrowth temperature. The minimum temperature may for example be a temperature beyond which heat equivalents are counted, for example 62° C. (corresponding to 143° F.) for the NSF3 standard or 65° C. for the EN ISO 15883 standard. The regrowth temperature may for example be any temperature which is selected to be higher than the minimum temperature. Preferably, the regrowth temperature may be selected so that delayed regrowth of apparently killed test germs or target germs and/or only partially killed test germs or target germs and/or at least temporarily inactivated test germs or target germs takes place at least in a reduced fashion. Reduced regrowth may in particular be taken to mean time-delayed regrowth, in particular very time-delayed regrowth, for example with a time lag of around several weeks, or to a greatly reduced extent.

In this method variant, for example, the counting of heat equivalents may be activated not until beyond or not until above a particular regrowth temperature, so that for example the counting of $A_0$ values does not take place until above this regrowth temperature. All normally counted heat equivalents in the range from the minimum temperature up to the defined regrowth temperature will therefore typically be left ignored.

The regrowth temperature may in principle be selected arbitrarily above the minimum temperature, and the regrowth temperature may for example be made dependent on one or more test germs and/or predetermined target germs. For example, the test germs used in the NSF3 standard and/or in the EN ISO 15883 standard may be employed. As an alternative, however, a user may be permitted to input one or more target germs to which, for example automatically, a regrowth temperature is assigned, for example by selecting a regrowth temperature assigned to the target germ from a list of regrowth temperatures. For example, this list may comprise an electronic table which may be stored in the controller. The target germ may for example, as explained in more detail below, comprise a pathogen with which the item to be cleaned is contaminated with high probability.

The at least one regrowth temperature may for example be determined by corresponding experiments, and for example stored for a multiplicity of target germs. For example, corresponding regrowth experiments may be carried out with a multiplicity of target germs, and the associated regrowth temperatures may be determined so that the regrowth takes place to a greatly reduced extent or not at all at these regrowth temperatures. The regrowth temperature may, however, also be selected according to expectation values or suppositions. For example, the regrowth temperature may be selected in a temperature interval of between 67° C. and 75° C., preferably in a temperature interval of between 70° C. and 87° C., and particularly preferably in a temperature interval of between 75° C. and 85° C.

As an alternative or addition to the method variants described above, in which the exceptional temperature range is selected at the lower end of the temperature scale beyond which heat equivalents are counted, the exceptional temperature range or, when a plurality of exceptional temperature ranges are specified one or more of these exceptional temperature ranges, may be selected in another way. For instance, the exceptional temperature range or one of the exceptional temperature ranges or several of the exceptional temperature ranges may also be selected so that at least one temperature range not assigned to the exceptional temperature range is arranged between the minimum temperature of a standard used for recording the heat equivalents (for example again the NSF3 standard and/or the EN ISO 15883 standard) and the starting temperature of the exceptional temperature range. In other words, the exceptional temperature range may be selected so that the counting of the heat equivalents is suspended for a particular exceptional temperature range. For example, the counting of $A_0$ values may be suspended in the exceptional temperature range, so that the heat equivalents normally counted in this range remain ignored for the cumulative heat equivalents.

As explained above, in particular a minimum disinfection effect may be achieved by the cumulative heat equivalents. This minimum disinfection effect may for example comprise a target disinfection effect, the target disinfection effect comprising a minimum sum of heat equivalents. The method may then for example be carried out at least until the summation of the heat equivalents yields the said minimum sum. For example, the target disinfection effect may be specified by a user and/or another computer or another computer network, for example via the interface described above.

Besides the aforementioned temperature, other values may also be recorded, for example by the cleaning device and/or the controller of the cleaning device, and may likewise be taken into account when selecting the compensation function. For example, other influencing values, in addition to the temperature at which the heat equivalents are recorded, may also have an influence on the disinfection effect, in particular the long-term disinfection effect. In particular a gradient of the temperature may play a special role, in particular a temporal gradient and/or a spatial gradient. For example, a "lag of regrowth effect" may be dependent on a temporal and/or spatial gradient of the temperature, in particular a temporal gradient, for example a rapid temperature change in comparison with a slow temperature change. For example, the regrowth effect may occur more greatly with an increasing gradient. Accordingly, for example, the compensation function may likewise be adapted to this gradient. For example, low temperatures may remain ignored to a greater extent with an increasing gradient, so that for example in one or both of the method variants described above the regrowth temperature may be placed higher with an increasing gradient of the temperature. This may, for example, in turn be done by automatic allocation, for example by assigning the regrowth temperature to the gradient by means of an automatic selection, for example from an electronic table. The regrowth temperature may thus be dependent on one or more values, for example at least one target germ and/or at least one gradient and/or other recorded measurement values. For example, a number of compensation functions may be specified, automatic allocation being carried out according to the recorded values, for example in the controller. As an alternative or in addition, as described above, the allocation or selection of the at least one compensation function may also be carried out while taking into account at least one information item concerning at least one target germ, with which the item to be cleaned could be contaminated.

The cleaning device may comprise corresponding devices for carrying out the method in one or more of the variants described above. In particular, the cleaning device may be adapted to permit a user and/or an external data-processing device to input one or more values. For example, these may be a compensation function and/or an exceptional temperature range and/or a target germ with which the item to be cleaned could be contaminated, and/or a storage time to be expected after cleaning for the item to be cleaned and/or combinations of the said and/or other values. As explained above, the input may for example be carried out via an input/output interface. The storage time to be expected may, for example, be taken into account in as much as the item to be cleaned, which in any event will only be stored for a relatively short period of time before next use, is treated with a lower regrowth temperature. For example, "lag of regrowth effects", in which regrowth of the vitality of the target germs could not occur until long after expected reuse, may be taken into account so that for example a low regrowth temperature is selected. If longer storage of the item to be cleaned is planned, however, then for example higher regrowth temperatures may be provided.

The proposed method and the proposed cleaning device have many advantages over known methods and devices. In contrast to known rigid methods and devices, which for example work exactly according to predetermined hygiene standards, the proposed method and the proposed cleaning device can react flexibly to the actual circumstances and, beyond a minimum hygiene effect, also ensure long-term hygiene effects. Influencing values, for example the temperature and/or the temperature gradient and/or other values, may for example be recorded as calibration values in order optionally to be incorporated into the compensation function, for example into calculation and/or filtering. The influence of such additional parameters is, for example, known from the field of pasteurization. The compensation function in the cleaning device may, for example, be configured so that the correction is commensurately greater as the gradient of the temperature becomes greater. For example, software of the controller may be adapted in order to handle such influencing values. Since flexible input of the compensation function is possible, a regular and/or intermittent update of the controller may be carried out, for example when further scientific discoveries are available. Implementation of parameter sets differentiated according to microorganism classes may also be carried out, for example through the input of one or more of the target germs described above. The proposed method can also be implemented straightforwardly in already existing controllers, by correspondingly adapting them with program technology. The method may for example be implemented as an option for software already provided, and/or established as a standard. At the same time, however, predetermined minimum hygienization can be ensured since the compensation described above can be carried out, for example, so that the item to be cleaned is hygienized at least according to a predetermined standard. In this way, for example, hygiene security and a disinfection level in relation to the conventional $A_0$ value method can be ensured or even increased, since for example it is merely necessary that thermoequivalents normally also counted can be left out of the cumulation by the compensation function. The modification of known cleaning devices can therefore be adapted so that they satisfy acknowledged standards as before.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
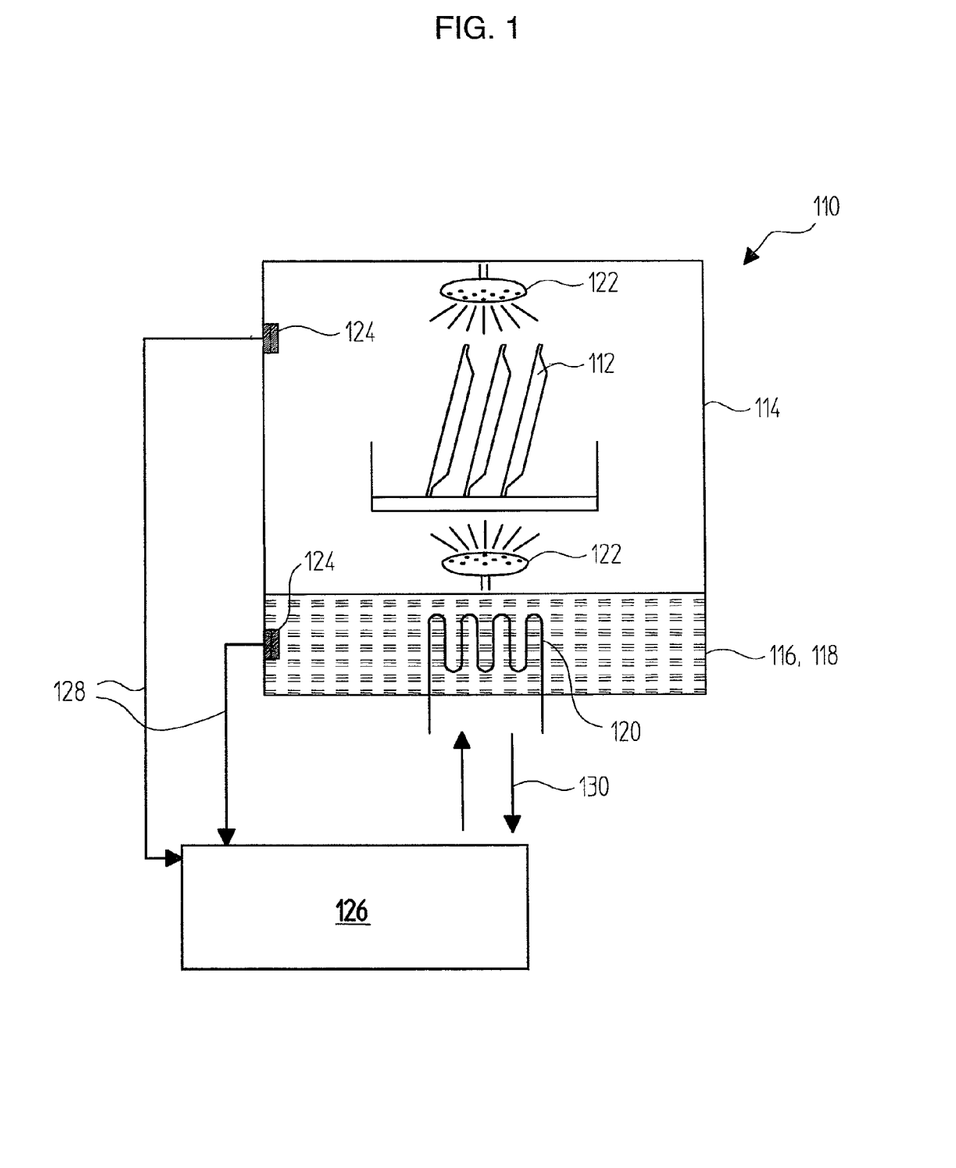
FIG. 1 shows an exemplary embodiment of a cleaning device according to the invention.

FIG. 1 shows in a simplified form an exemplary embodiment of a cleaning device 110 according to the invention in a schematic representation. The cleaning device 110 is used to clean items 112 to be cleaned, indicated in a stylized fashion, in a cleaning chamber 114 by using a cleaning fluid 116. For example, this item 112 to be cleaned may be a chamberpot, bedpan, urine bottle, night-time utensil or another item to be cleaned. Other types of items 112 to be cleaned may, however, also be used in principle. The cleaning fluid 116 is partially held in a tank 118 and heated by means of a heating device 120. The cleaning fluid 116 is sprayed onto the item 112 to be cleaned by means of a nozzle system 122. The temperature of the item 112 to be cleaned and/or the cleaning fluid 116 is monitored by means of one or more temperature sensors 124.

In the cleaning device 110 represented, the cleaning fluid 116 is indicated as a liquid cleaning fluid. As an alternative or in addition, however, a gaseous cleaning fluid 116 may also be used, for example hot steam for hygienizing the item 112 to be cleaned. In this case, the at least one temperature sensor 124 may for example also monitor a steam temperature inside the cleaning chamber 114. As an alternative or in addition, the cleaning sensor 124 may also for example monitor a temperature directly on the item 112 to be cleaned, by means of an infrared measurement. Different embodiments are possible and known from the prior art.

The cleaning device 110 furthermore comprises a controller 126, which can for example interrogate signals of the temperature sensors 124 via control lines 128 and/or control and/or regulate other components of the cleaning device 110 via at least one interface 130.

Figure 2A:
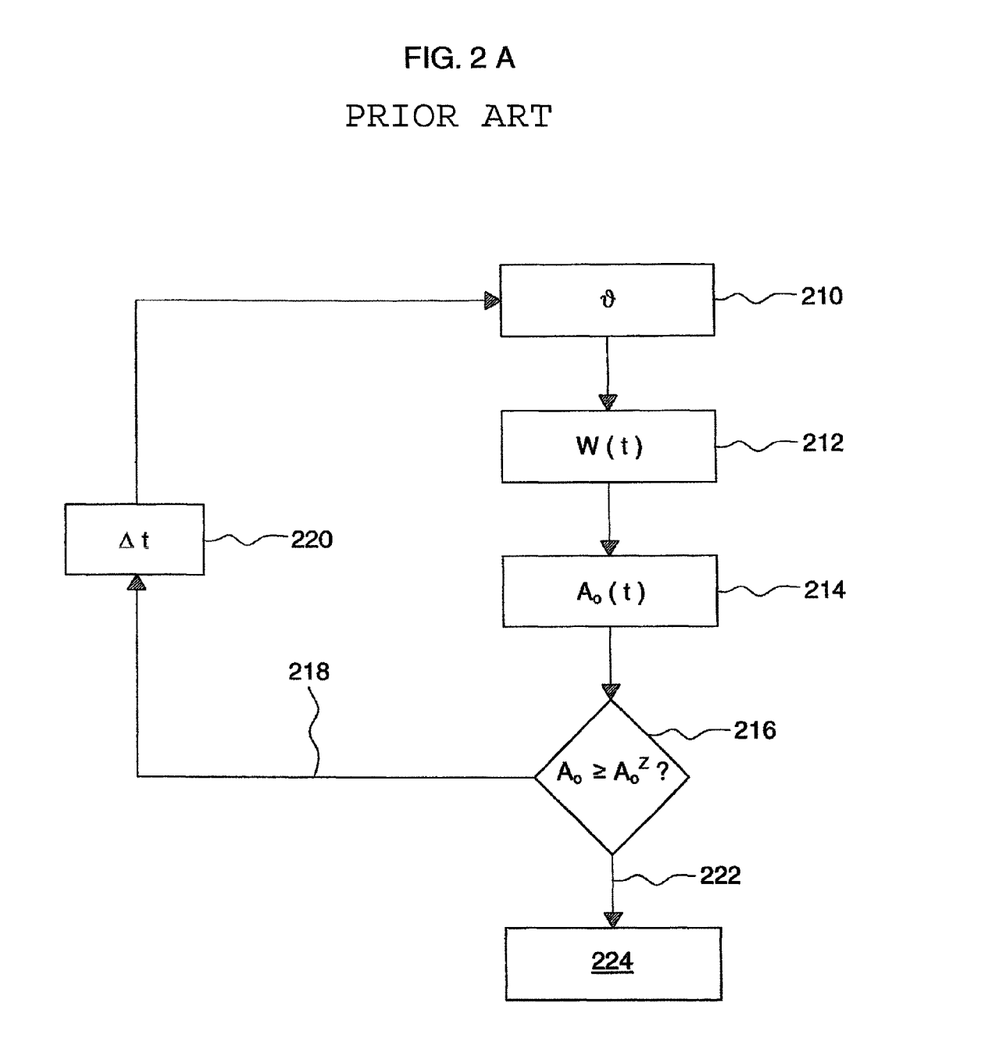
FIG. 2A shows a schematic flow chart of a method according to the prior art.
Figure 2B:
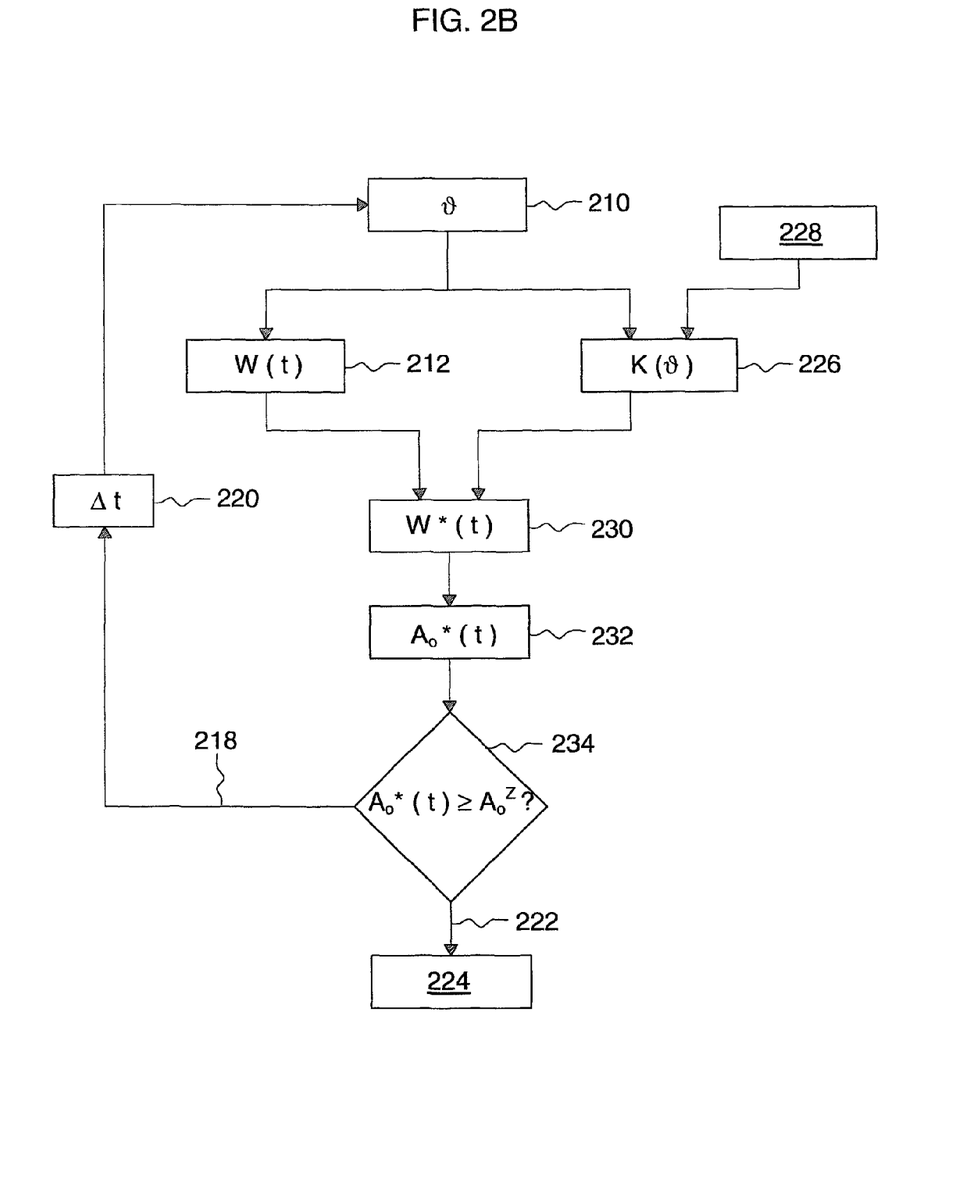
FIG. 2B shows a schematic flow chart of a method according to the invention.

FIGS. 2A and 2B represent flow charts of methods for cleaning items to be cleaned while ensuring a thermal hygiene effect. FIG. 2A shows a flow chart of a method corresponding to the prior art, whereas FIG. 2B shows an inventive modification of the method according to FIG. 2A. By way of example, it will be assumed below that the method according to FIG. 2A follows the standard EN ISO 15883, so that for example reference may be made to the definitions given in Annex A of this standard. Other standards may however also be used as an alternative or in addition, for example the NSF3 standard cited above.

First, the method corresponding to the prior art as referred to in FIG. 2A will be described. This method may, for example, be implemented in the controller 126 of a cleaning device 110 according to FIG. 1.

In a first method step (step 210), a temperature $\theta$ is recorded. From this temperature $\theta$, in a subsequent method step 212, a value is calculated which will generally be referred to here and below as a heat equivalent and which generally represents the function value of a monotonically increasing function, applied to the temperature $\theta$. In the standard EN ISO 15883, this heat equivalent, which will be denoted below by the letter W, is determined at a time t according to the following formula:

$$W(t) = 10^{(\theta-80)/z} \quad (1).$$

In this case the temperature $\theta$ is indicated in °C., and only temperatures $\theta$ of at least 65° C. are taken into account. The value z (z value) is according to EN ISO 15883 the temperature change in K which is necessary in order to achieve a 10-fold change of the microbial inactivation rate in a disinfection process with wet heat. This z value may be dependent on particular germs, for example the target germs specified in the method.

In another method step 214, the heat equivalents are cumulated over time. This may for example be done continuously by integration or, as in EN ISO 15883, over discrete time segments which are established in EN ISO 15883 as $\Delta t=1$ s. Other time intervals and/or time intervals of different length may, however, also be used. According to EN ISO 15883, this cumulation to give the so-called $A_0$ value is carried out according to the following formula:

$$A_0 = \sum_t W(t) \cdot \Delta t. \quad (2)$$

In method step 216, a query is made as to whether the cumulative heat equivalents have reached a minimum sum, which is denoted here by $A_0{}^z$. If this is not the case (branch 218 in FIG. 2A), then the measurement is repeated after a waiting time of $\Delta t$ (step 220 in FIG. 2A), so that method steps 210 to 216 are carried out again. If however the minimum sum $A_0{}^z$ is reached (branch 222 in FIG. 2A), then the program can be ended (step 224). This conventional method therefore ensures that the item 112 to be cleaned is exposed to a minimum sum $A_0{}^z$ of heat equivalents.

Figure 3:
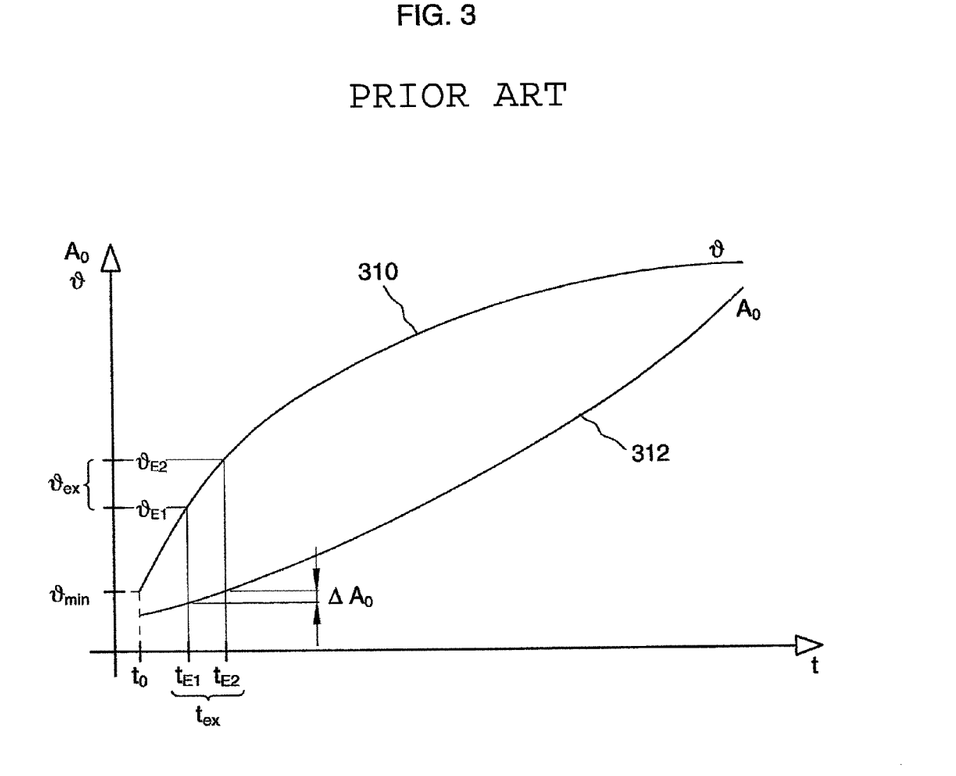
FIG. 3 shows a heating curve and cumulative heat equivalents according to a conventional method.

In FIG. 3, a typical heating curve (curve 310, corresponding to the axis designation $\theta$) of items 112 to be cleaned is plotted as a function of time t. The chronological development of the cumulative heat equivalents is furthermore plotted in a curve 312 (axis designation $A_0$).

It can be seen from the representation that, at a time $t_0$, the item 112 to be cleaned reaches a minimum temperature $\theta_{min}$ beyond which the heat equivalents are counted according to the respective standard. For EN ISO 15883, this is for example a temperature of 65° C. The $A_0$ curve 312 assumes the value 0 at this time, and from then on it grows monotonically. Thus, the $A_0$ value increases for example by the amount $\Delta A_0$ in an interval between $\theta_{E1}$, and $\theta_{E2}$.

The method shown in FIG. 2A, however, does not under certain circumstances take into account "lag of growth effects". FIG. 2B accordingly represents an inventive modification of the method, in which the temperature $\theta$ is likewise initially determined, again in method step 212, during a process of cleaning the item 112 to be cleaned. From this temperature $\theta$, in method step 212, the heat equivalent W(t) is again determined similarly as in FIG. 2A, in which case for example the aforementioned Formula (1) may again be used.

Simultaneously with or at a time offset from method step 212, a compensation function K is however determined in method step 226. The function value of this compensation function K is dependent on the temperature $\theta$. At the same time, however, the compensation function K may also be dependent on one or more target germs, with which the item 112 is contaminated with high probability. The input of such target germs is symbolized by method step 228 in FIG. 2B.

The compensation function provides a weighting of the heat equivalents W(t), which is intended to avoid "lag of regrowth effects". For example temperature ranges in which disinfection contributes to the count of the heat equivalents $A_0$, but for which "lag of regrowth effects" can however occur later with a delay, are deliberately weighted lower or even entirely eliminated from the count. Accordingly, the compensation function K may involve simple multiplication of the heat equivalents W(t) from method step 212 by the compensation function K. More complex compensation functions, which act on W(t), are however also possible. With simple multiplication, for example, as indicated in FIG. 2B, in method step 230 weighting of the heat equivalent W(t) may be carried out to form a weighted heat equivalent W*(t), for example according to the following formula:

$$W^*(t,\theta) = (\theta) \cdot W(t) \qquad (3).$$

In method step 232, the weighted heat equivalents W*(t) from method step 230 are cumulated, similarly as in method step 214 in FIG. 2A. This is done for example according to the following formula:

$$A_0^* = \sum_t W^*(t) \cdot \Delta t. \qquad (4)$$

Subsequently, in method step 234, similarly as in method step 216 in FIG. 2A, a query is made as to whether the cumulative weighted heat equivalents $A_0^*$ have already reached the minimum sum $A_0^z$. If this is not the case (branch 218), then the method may be repeated with the measurement and cumulation after a waiting time Δt (step 220). Not necessarily all the method steps have to be repeated in this case. For example, the input of a target germ in step 228, which in any case is optional, does not necessarily have to be repeated; rather, it is merely necessary to determine a function value K(θ) of the newly measured temperature θ in step 226. If however the minimum sum $A_0^z$ is reached (branch 222 in FIG. 2B), then the method may in principle be ended.

Figure 4:
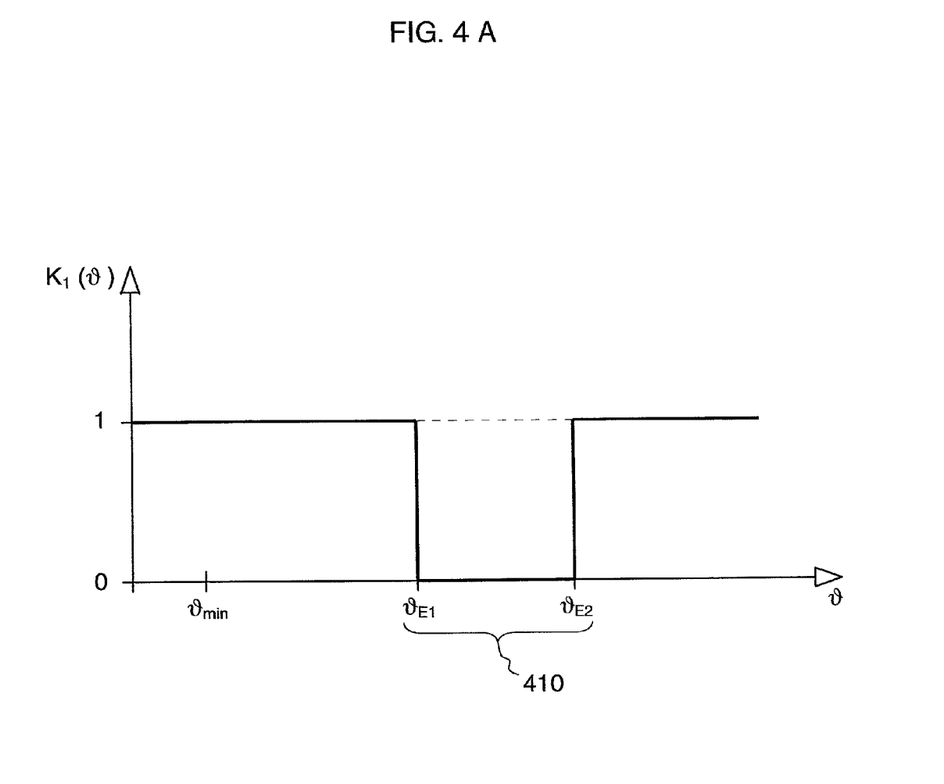
FIG. 4A shows a compensation function according to a first exemplary embodiment of a method according to the invention.
FIG. 4B shows a cumulative heat equivalent according to the first embodiment of the method according to the invention.

The compensation function K(θ) may in principle, as explained above, eliminate temperature ranges which according to conventional methods contribute to the cumulative heat equivalents $A_0$, but which lead however to less efficient hygienization in respect of the "lag of regrowth effect". FIG. 4A represents a first exemplary embodiment of a compensation function $K_1(\theta)$ as a function of the temperature θ of the item 112 to be cleaned, in which an exceptional temperature range (symbolically denoted by the reference 410 in FIG. 4A) is not taken into account for calculating the cumulative heat equivalents. This exceptional temperature range extends between the temperatures $\theta_{E1}$ and $\theta_{E2}$, both of which lie above the minimum temperature $\theta_{min}$. For example, $\theta_{E1}$ could be selected between 65° C. and 75° C. and $\theta_{E2}$ between 70° C. and 80° C.

Mathematically, the compensation function $K_1$ may be described in that it assumes the value 1 for the values outside the exceptional temperature range 410 and the value 0 for values inside the exceptional temperature range:

$$K_1(\theta) = 0 \text{ for } \theta_{E1} \le \theta \le \theta_{E2} \qquad (5a)$$

$$K_1(\theta) = 1 \text{ otherwise.} \qquad (5b)$$

On the basis of this compensation function $K_1$, FIG. 4B represents the cumulative weighted heat equivalent $A_0^*$, calculated according to Equation (4), as a function of time t. The heating curve 310 in FIG. 3, which reaches the minimum temperature $\theta_{min}$ at time $t_0$ and the temperatures $\theta_{E1}$ and $\theta_{E2}$ respectively at times $t_{E1}$ and $t_{E2}$, again represents the starting point. The heating curve in FIG. 4B is, like the heating curve in FIG. 3, represented as a continuous curve even though this curve theoretically represents a discontinuous function with time segments of 1 s. In the limiting case of infinitely small time segments Δt (i.e. integration as a function of time), however, this curve is for example continuous.

As may be seen from the representation in FIG. 4B, the cumulative weighted heat equivalent $A_0^*$ does not change in the time window between $t_{E1}$ and $t_{E2}$, i.e. while the temperature of the item 112 to be cleaned lies within the exceptional temperature range 410 in FIG. 4A. Only when the upper limit $\theta_{E2}$ of the exceptional temperature range 110 is exceeded does the cumulative weighted heat equivalent curve increase again.

Other configurations of the compensation curve K(θ) are however possible, as explained above. For instance, this compensation function may also be a functional of the function W(t).

Figure 5:
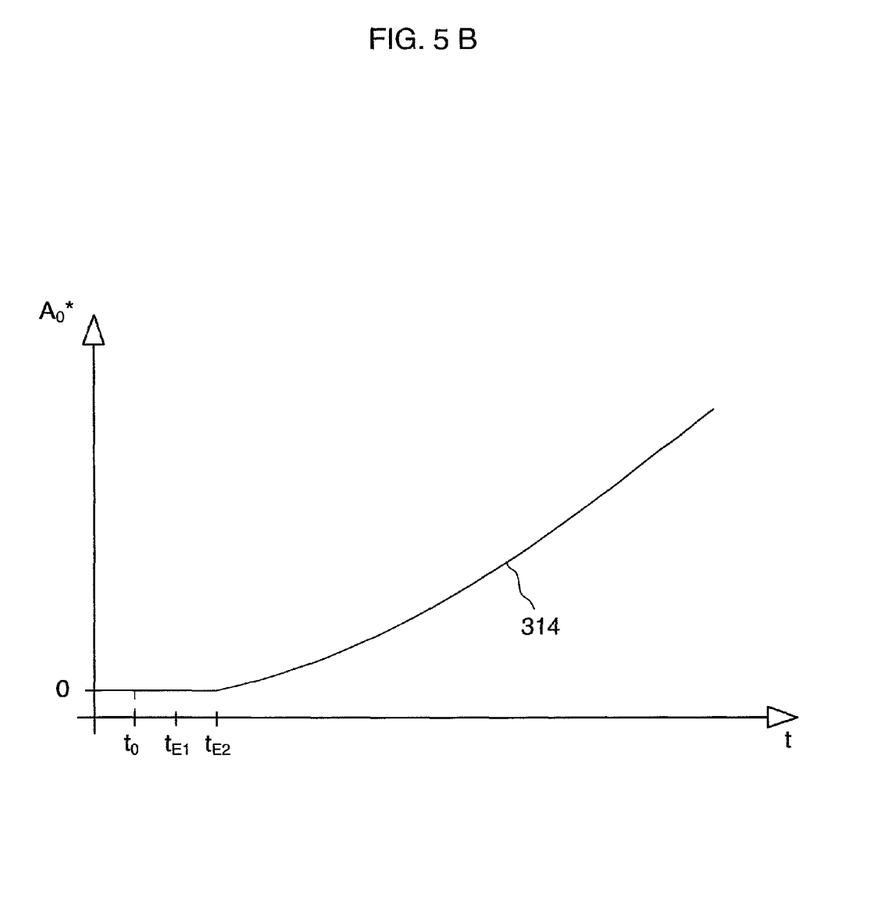
FIG. 5A shows a compensation function according to a second exemplary embodiment of a method according to the invention.
FIG. 5B shows cumulative heat equivalents according to the second exemplary embodiment of the method according to the invention.
Figure 5A:
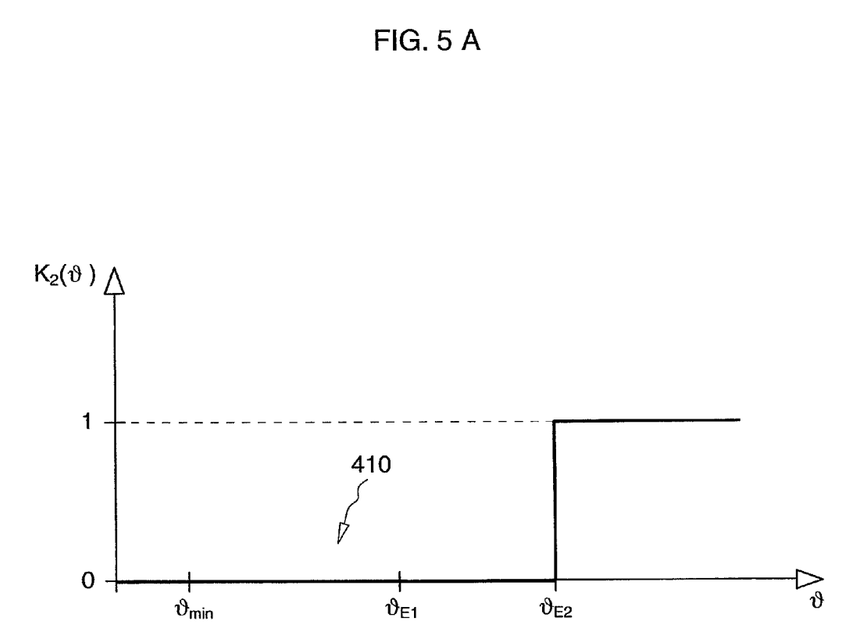

FIGS. 5A and 5B show a second exemplary embodiment of a method according to the invention in a representation similar to FIGS. 4A and 4B. This example represents a limiting case in which the lower limit of the exceptional temperature range is shifted to $\theta_{min}$, i.e. the minimum temperature for the standard being used, or even to lower temperatures. Physically, this no longer makes a difference since shifts of the lower interval limit of the exceptional temperature range 410 to temperatures below $\theta_{min}$ do not have an effect on the results, since no heat equivalents would be cumulated anyway below $\theta_{min}$. The upper limit of the exceptional temperature range 410, i.e. the temperature $\theta_{E2}$, may also be referred to as the regrowth temperature since, for example, this temperature can be selected so that delayed regrowth of apparently killed test germs and/or at least one target germ takes place at least in a reduced fashion. For example, this temperature may lie at 80° C. or higher.

On the basis of the heating curve 310 in FIG. 3, FIG. 5B is in turn a curve of the cumulative weighted heat equivalents $A_0^*$ for the compensation function $K_2$ in FIG. 5A. As in FIG. 4B, the curve of the cumulative weighted heat equivalents is again denoted by the reference number 314.

The curve 314 in FIG. 5B shows that up to the time $t_{E2}$, at which have the heating curve 310 in FIG. 3 reaches the regrowth temperature $\theta_{E2}$, no heat equivalents are cumulated. Beyond this time, the curve 314 increases and heat equivalents are cumulated.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method for cleaning and/or disinfecting an item to be cleaned, the method comprising:

exposing the item to be cleaned to at least one cleaning fluid;

recording heat equivalents to which the item to be cleaned is exposed;

summing the heat equivalents;

weighting the heat equivalents with a compensation function during the summation of the heat equivalents, the compensation function being a function of the temperature at which the heat equivalents were recorded; and adapting the compensation function to provide heat equivalents recorded in at least one exceptional temperature range with a lower weighting than heat equivalents recorded in other temperature ranges, the compensation function being selected while taking into account at least one information item concerning at least one target germ, with which the item to be cleaned could be contaminated, wherein the compensation function is adapted so that the exceptional temperature range extends between a minimum temperature of a standard used for recording the heat equivalents and at least one predetermined regrowth temperature, the regrowth-temperature being higher than the minimum temperature, wherein the regrowth temperature is selected so that the delayed regrowth of killed, partially killed, at least temporarily inactivated test germs, or at least one predetermined target germ takes place at least in reduced fashion, and wherein said recording heat equivalents is based on a temperature of the at least one cleaning fluid or a temperature directly on the item to be cleaned or that of steam in an interior of a cleaning chamber.

2. The method according to claim 1, wherein the compensation function is adapted so that heat equivalents which have been recorded in the at least one exceptional temperature range are not taken into account in the summation.

3. The method according to claim 1, wherein the compensation function assumes a value of less than one or a value of zero for temperatures inside the exceptional temperature range, and the value of one for temperatures outside the exceptional temperature range.

4. The method according to claim 1, wherein the regrowth temperature is selected in a temperature interval of between 67° C. and 95° C.

5. The method according to claim 1, wherein the exceptional temperature range is selected so that at least one temperature range not assigned to the exceptional temperature range is arranged between a minimum temperature of a standard used for recording the heat equivalents and a starting temperature of the exceptional temperature range.

6. The method according to claim 1, wherein the heat equivalents are recorded according to NSF/ANSI 3 standard or according to EN ISO 15883 standard.

7. The method according to claim 1, wherein at least one target disinfection effect is specified, the target disinfection effect comprising a minimum sum of heat equivalents, and wherein the method is carried out at least until the summation yields the minimum sum.

8. The method according to claim 1, wherein at least one gradient of the temperature is furthermore determined.

9. The method according to claim 8, wherein the compensation function is selected while taking the gradient into account.

10. A cleaning device for cleaning and/or disinfecting an item to be cleaned, the cleaning device comprising at least one controller for controlling a cleaning process and a temperature sensor for monitoring a temperature inside a cleaning chamber, wherein the cleaning device is configured to perform a method comprising:

exposing the item to be cleaned to at least one cleaning fluid;

recording heat equivalents to which the item to be cleaned is exposed;

summing the heat equivalents;

weighting the heat equivalents with a compensation function during the summation of the heat equivalents, the compensation function being a function of the temperature inside the cleaning chamber at which the heat equivalents were recorded; and adapting the compensation function to provide heat equivalents recorded in at least one exceptional temperature range with a lower weighting than heat equivalents recorded in other temperature ranges, the compensation function being selected while taking into account at least one information item concerning at least one target germ, with which the item to be cleaned could be contaminated, wherein the compensation function is adapted so that the exceptional temperature range extends between a minimum temperature of a standard used for recording the heat equivalents and at least one predetermined regrowth temperature, the regrowth-temperature being higher than the minimum temperature, wherein the regrowth temperature is selected so that the delayed regrowth of killed, partially killed, at least temporarily inactivated test germs, or at least one predetermined target germ takes place at least in reduced fashion, and wherein said recording heat equivalents is based on a temperature of the at least one cleaning fluid or a temperature directly on the item to be cleaned or that of steam in an interior of the cleaning chamber.

11. The cleaning device according to claim 10, wherein the cleaning device is configured to permit a user and/or an external data-processing device to input one or more of the following values: a compensation function; an exceptional temperature range; a target germ with which the item to be cleaned could be contaminated; and/or a storage time to be expected after cleaning for the item to be cleaned.

12. A computer program having program code for carrying out a method comprising:

exposing the item to be cleaned to at least one cleaning fluid;

recording heat equivalents to which the item to be cleaned is exposed;

summing the heat equivalents;

weighting the heat equivalents with a compensation function during the summation of the heat equivalents, the compensation function being a function of the temperature at which the heat equivalents were recorded; and adapting the compensation function to provide heat equivalents recorded in at least one exceptional temperature range with a lower weighting than heat equivalents recorded in other temperature ranges when the program is run on a computer, the compensation function being selected while taking into account at least one information item concerning at least one target germ, with which the item to be cleaned could be contaminated, wherein the compensation function is adapted so that the exceptional temperature range extends between a minimum temperature of a standard used for recording the heat equivalents and at least one predetermined regrowth temperature, the regrowth-temperature being higher than the minimum temperature, wherein the regrowth temperature is selected so that the delayed regrowth of killed, partially killed, at least temporarily inactivated test germs, or at least one predetermined target germ takes place at least in reduced fashion, and wherein said recording heat equivalents is based on a temperature of the at least one cleaning fluid or a temperature directly on the item to be cleaned or that of steam in an interior of a cleaning chamber.

13. A computer program according to claim 12, wherein the program code is stored on a machine-readable medium.

14. The method according to claim 1, wherein the regrowth temperature is selected in a temperature interval of between 70° C. and 87° C.

15. The method according to claim 1, wherein the regrowth temperature is selected in a temperature interval of between 75° C. and 85° C.

* * * * *